United States Patent [19]

Boyd

[11] Patent Number: 4,613,328
[45] Date of Patent: Sep. 23, 1986

[54] BIO-MEDICAL INJECTOR APPARATUS

[76] Inventor: Cecil Boyd, P.O. Box 428, Neosho, Mo. 64850

[21] Appl. No.: 663,132

[22] Filed: Oct. 22, 1984

[51] Int. Cl.$^4$ .............................................. A61M 5/20
[52] U.S. Cl. .................................... 604/156; 604/245; 604/900; 604/131; 128/633; 128/638; 128/DIG. 1; 128/DIG. 13
[58] Field of Search ................... 604/152–156, 604/131, 20, 21, 245, 158, 168, 900; 128/633, 634, 635, 638, 766, 771, DIG. 1, DIG. 13

[56] References Cited

U.S. PATENT DOCUMENTS

| | | | |
|---|---|---|---|
| 3,964,481 | 6/1976 | Gourlandt et al. | 604/156 |
| 4,181,610 | 1/1980 | Shintani et al. | 604/245 |
| 4,276,879 | 7/1981 | Yiournas | 604/156 |
| 4,515,590 | 5/1985 | Daniel | 604/156 |
| 4,553,552 | 11/1985 | Valdespino et al. | 128/771 |

Primary Examiner—Leo P. Picard
Attorney, Agent, or Firm—Head, Johnson & Stevenson

[57] ABSTRACT

A bio-medical injector apparatus comprising a base unit having a skin engaging portion disposed at an angular orientation with respect to the longitudinal axis of the base unit for supporting and maintaining a hypodermic needle at an optimum angular orientation for effecting an injection procedure, a carriage assembly reciprocally mounted on the base unit and carrying the hypodermic needle simultaneously therewith, a motor drive unit operably connected with the hypodermic needle for the preloading thereof with a suitable medication, a solenoid secured to the base unit and operably connected with the carriage assembly for a controlled reciprocation thereof for effecting the injection operation of the needle, and an electronic circuitry operably connected between a power supply and the motor drive and the solenoid for creating the logic necessary to perform the functions of the injector apparatus.

6 Claims, 4 Drawing Figures

BIO-MEDICAL INJECTOR APPARATUS

BACKGROUND OF THE INVENTION

1. Field of the Invention

This invention relates to improvements to medical equipment and more particularly, but not by way of limitation, to a bio-medical injector means.

2. Description of the Prior Art

At the present time there are three basic types of injections given with a hypodermic apparatus. One type involves the injection of the hypodermic into the fatty area or fatty tissues of the body, and is commonly referred to as a "Sub-Q" injection. Another type is the application of the hypodermic apparatus directly into a vein, and this is commonly known as an "IV" or an intravenous injection. This third of the basic types of hypodermic usage is the application of the apparatus directly into a muscular area, and this is usually referred to as an "IM" or intramuscular injection. In many instances, a patient requiring any of these basic types of injection medication is required to utilize a self-injection method, as for example, a diabetic person, or the like. The application of many of these injections is difficult, painful and unpleasant, and as a result the medication may not be rendered correctly or at sufficient time intervals, which may have undesirable consequences for the patient or person required to use self-injection techniques. Many attempts have been made to provide improved injecting apparatus for facilitating the overall injection operations, whether or not the operation is a self-injected one. Examples of such solutions to the problems are shown in the Kayden Pat. No. 2,295,849, issued Sept. 15, 1942, and entitled "Attachment for Hypodermic Syringes;" the May Pat. No. 2,679,843, issued June 1, 1954, and entitled "Injection Apparatus;" the Tibbs Pat. No. 3,702,608, issued Nov. 14, 1972, and entitled "Painless Injection Device with Powered Plunger;" The Steiner Pat. No. 3,702,609, issued Nov. 14, 1972, and entitled "Hypodermic Syringes, in Particular Self-Injecting Syringes;" The Haller Pat. No. 4,067,334, issued Jan. 10, 1978, and entitled "Self-Injecting Hypodermic Syringe Device;" the Wagner Pat. No. 4,114,619, issued Sept. 19, 1978, and entitled "Automatic Injecting Apparatus;" The Tischlinger Pat. No. 4,178,928, issued Dec. 18, 1979, and entitled "Self Injector;" the Harris Pat. No. 4,185,627, issued Jan. 29, 1980, and entitled "Device for Inserting Syringe;" The Haller Pat. No. 4,198,975, issued April 22, 1980, and entitled "Self-Injecting Hypodermic Syringe Device;" the Wardlaw Pat. No. 4,227,528, issued Oct. 14, 1980, and entitled "Automatic Disposable Hypodermic Syringe;" the Rocker Pat. No. 4,231,368, issued Nov. 4, 1980, and entitled "Device for Intramuscular Injections, Especially of Insulin;" the Becker Pat. No. 4,333,459, issued June 8, 1982, and entitled "Intramuscular Injection Device Suitable for Insulin Injections;" and the Reynolds Pat. No. 4,407,283, issued Oct. 4, 1983, and entitled "Self-Injecting Syringe." Although some of the foregoing patents utilize a relatively small amount of electrical design in the construction and operation thereof, none provide any "electronic brain" which may greatly facilitate the overall use and/or operation of a bio-medical injection apparatus.

SUMMARY OF THE INVENTION

The present invention contemplates a novel bio-medical hypodermic or injection apparatus comprising a base unit for housing the components of the apparatus, with the possible exception of the power supply, and which is positioned and maintained in contact with the skin during the injection operation. A carriage means is movably or slidably mounted on the base unit and contains or houses the hypodermic needle. The prepared hypodermic needle is secured to the carriage in such a manner that it cannot move independently of the carriage. The sliding movement of the carriage causes the needle to penetrate the skin. The movement is transmitted to the carriage by a solenoid means, and a motor drive means is installed within or on the carriage and is operational for the control of the plunger of the hypodermic which performs the actual injection of the medication. The power supply for the apparatus is the electronic circuitry which provides electrical energy to the solenoid, motor drive and the "brain". The "brain" comprises a plurality of electronic components which collectively create the logic required for the performance of the functions during the operation of the novel bio-medical injection apparatus.

The device received or supports a hypodermic needle at an angular moment of approximately forty five degrees with respect to the surface wherein the needle is to be injected. In one particular mode of operation, the hpodermic is thrust into the fatty tissue of the body, as in the manner of substantially any injection procedure, by means of the action of the novel device itself. This step is followed by the aspiration (or pulling outward on the hypodermic plunger) of the needle in order to check for the presence of blood thereon. A sensor means provided on the device monitors this operation, and in the event blood is present, indicating that the needle had encountered or punctured a vein, then the device would abort the injection procedure. If blood is not present the next step in the procedure is the actual injection itself. All of these processes or steps are controlled by the "brain" of the device. The novel bio-medical injection apparatus is simple and efficient in operation and economical and durable in construction.

DETAILED DESCRIPTION OF THE PREFERRED EMBODIMENT

Figure 1:
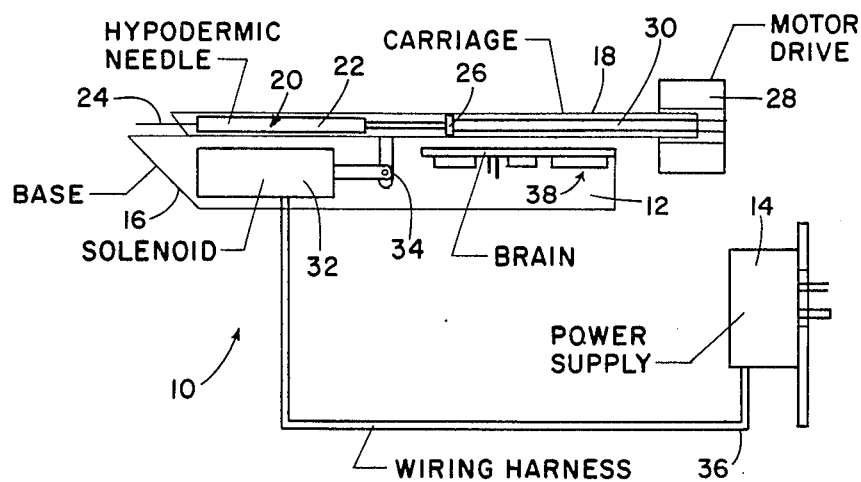
FIG. 1 is a schematic side elevational view of a bio-medical injection apparatus embodying the invention.
Figure 2:
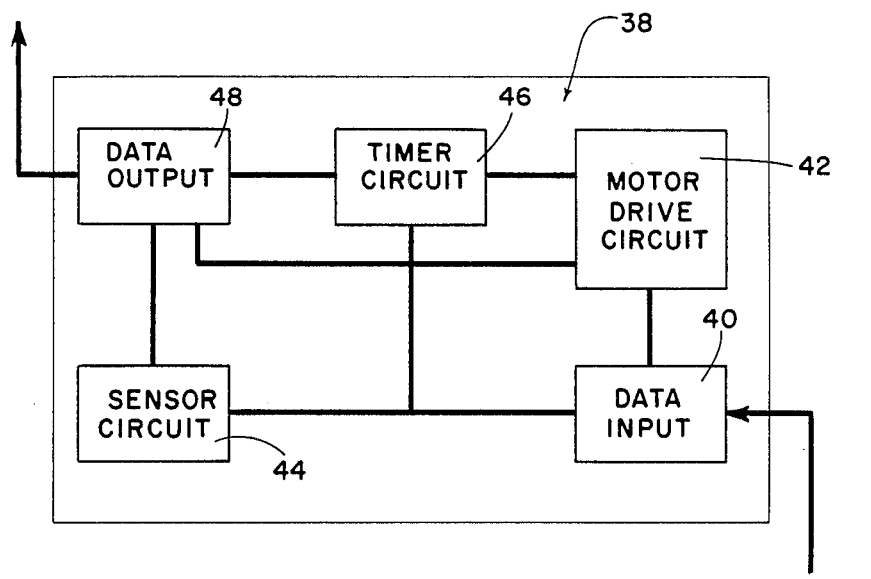
FIG. 2 is a block diagram of the "brain" portion of a bio-medical injection apparatus embodying the invention.

Referring to the drawings in detail, reference character 10 generally indicates a bio-medical injection apparatus comprising a base unit which supports or houses all of the components of the device, with the possible exception of a power supply 14. The base means or unit 12 may be of any suitable construction and configuration, and may be provided with a planar surface 16 disposed at an angle with respect to the longitudinal axis of the base unit. It is preferable that the angular orientation of the surface 16 be at approximately forty five degrees with respect to the longitudinal axis of the base 12, but there is no intention of limiting the invention to that particular configuration. The surface 16 is adapted to be placed adjacent the skin at the area of a human body (not shown) wherein a medical injection operation is to take place, as will be hereinafter set forth.

A carriage mechanism 18 is slidably or movably secured on the base unit 12 for reciprocation with respect thereto. The carriage 18 may be secured to the base 12 in any suitable or well known manner, such as by a track means (not shown), cooperating grooves (not shown), or the like, wherein the movement of the carriage 18 is along a predetermined or preselected linear path.

A hypodermic needle means 20 is removably secured to the carriage 18 in any suitable or well known manner (not shown) and is secured thereon in such a manner that the needle means 20 is not movable independently of the carriage means 18. Of course, the needle means is initially prepared for the injection operation, such as by being provided with a charge or quantity of the required medical dosage, and then secured on the carriage means 18. The needle means preferably includes the usual housing 22 adapted for receiving the medical dosage therein, as is well known, and a hollow needle member 24 which penetrates the skin during an injection operation. A reciprocal plunger means 26 is provided for the cartridge or housing 22, and is operable in the well known manner for drawing or pulling the medical dosage into the housing 22.

The reciprocal plunger means 26 may be operably connected with a suitable motor drive means 28 in any well known manner, such as by a linkage means or shaft 30 whereby the plunger 26 may be reciprocated for ejecting the contents of the housing 22 through the needle 24 during an injection procedure. The particular motor drive means 28 may be a digital linear actuator comprising a stepper motor (not shown) having a hollow rotor (not shown) through which the shaft 30 passes. The shaft 30, in this particular instance, is a threaded shaft and as the rotor, which is also threaded, rotates it causes the threaded shaft 30 to move in a linear direction. The outer end of the shaft 30 is suitably secured to or connected with the plunger means 26 to provide a controlled reciprocation therefor. As hereinbefore set forth, the motor drive means is secured to or carried by the carriage means 18 and moves simultaneously therewith when the carriage is reciprocated with respect to the base means 12, as will be hereinafter set forth.

A solenoid 32, or the like, is suitably mounted on the base 12 and is operably connected with the carriage 18 in any well known manner, such as by a linkage assembly 34, for providing the reciprocation for the carriage and hypodermic needle means with respect to the base 12. The solenoid is in operable connection with the power supply 14 through a wiring harness means 36 whereby electrical energy is directed to the solenoid for actuation thereof. The energization or activation of the solenoid 32 moves the carriage assembly 18 and hypodermic needle means 20 in one direction along the longitudinal length of the base means 12, and deactivation of the solenoid 32 moves the carriage assembly 18 and hypodermic needle means 20 in an opposite direction along the base means.

A "brain" assembly 38 is interposed between the power supply 14 and all of the electrical components of the apparatus 10, i.e. the solenoid 32 and the motor drive 28. The "brain" assembly 38 comprises a data input circuitry 40 in operable connection with the power supply 14, a motor drive circuit 42, a sensor circuit 44 and a timer circuit 46. The sensor circuit is also in operable connection with the motor drive circuit 42. The timer circuit 46 is in operable connection with both the motor circuit 42 and the data output circuit 48. The data output circuit 48 is in operable connection with the solenoid 32 and the motor drive means 28. The components of the "brain" 38 collectively create the logic necessary to perform the functions of the apparatus 10.

The power supply 14 is the electronic circuitry which provides electrical energy to the solenoid 32, motor drive 28 and the "brain" assembly 38. The power supply preferably performs its functions through a transformer circuit plugged directly into the usual wall socket (not shown) and/or through the use of a rechargable battery means (not shown). Thus, the apparatus 10 is of a portable construction which may be utilized at substantially any location wherein the user of the apparatus 10 is situated. The wiring harness 36 is the usual collection of electrical conduits or wires which connect the power supply 14 to the electrical components of the apparatus 10. Normally, the wiring harness will comprise no less than two wires and no more than ten individual wires, but there is no intention of limiting or establishing the number of wires required since the actual number of wires in the apparatus 10 is really insignificant.

In use of the apparatus 10, the plunger means 26 is actuated in the normal manner for filling the housing means 22 with the desired or required quantity of a medication dosage. The filled or prepared hypodermic needle assembly 20 may then be secured on the carriage 18 for reciprocal movement simultaneously therewith and connected with the motor drive means 28 as hereinbefore set forth. The surface 16 of the base unit 12 may be placed against the surface of the skin of the patient or user of the apparatus. Since the preferred angular orientation of the surface 16 with respect to the longitudinal axis of the base unit or base means 12 is forty five degrees, the angular orientation of the needle 24 with respect to the surface of the skin engaged by the surface 16 will be approximately forty-five degrees. This has been found to be an optimum position for the needle during an injection procedure.

The hypodermic needle may then be thrust into the fatty tissue of the body, as in any injection of this type, by means of the activation of the device 10 itself. This step is followed by the aspiration (or pulling outwardly of the plunger 26) of the needle 24 in order to check for the presence of blood thereon. The sensor circuit 44 monitors this operation, and in the event blood is present on the needle 24, indicating that the needle has inadvertently engaged or pierced a vein, then the continued actuation of the device 10 would be aborted. If no blood is sensed in the initial thrusting of the needle into the fatty tissue, then the apparatus 10 will automatically proceed with the actual injection step.

All of the operational steps of the apparatus 10 are controlled by the "brain" 38 or the electronic circuitry which is present in the device 10 itself. It is also preferable to include several "fail safe" self checks in the electronic circuitry of the apparatus 10 to assure that it does not malfunction. It is to be understood that it is not necessary for the unit or apparatus 10 to be totally automatic. In addition, it may be assembled or constructed in several modifications in order that it may be utilized in other industries or by individuals who require less automation or a manual unit of some kind.

Figure 3:
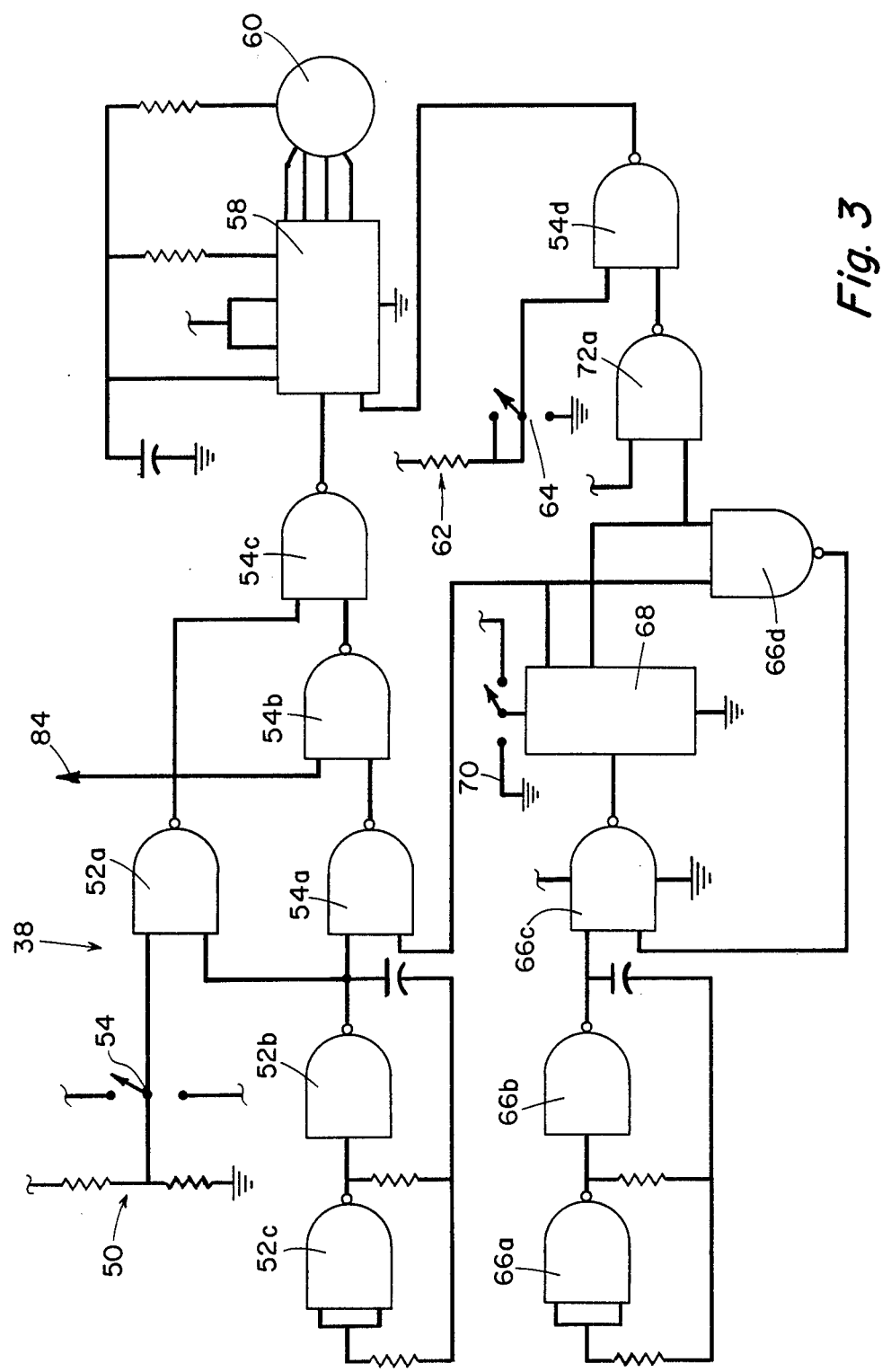
FIG. 3 illustrates a preferred electrical schematic diagram for the electronic brain of FIG. 1
Figure 4:
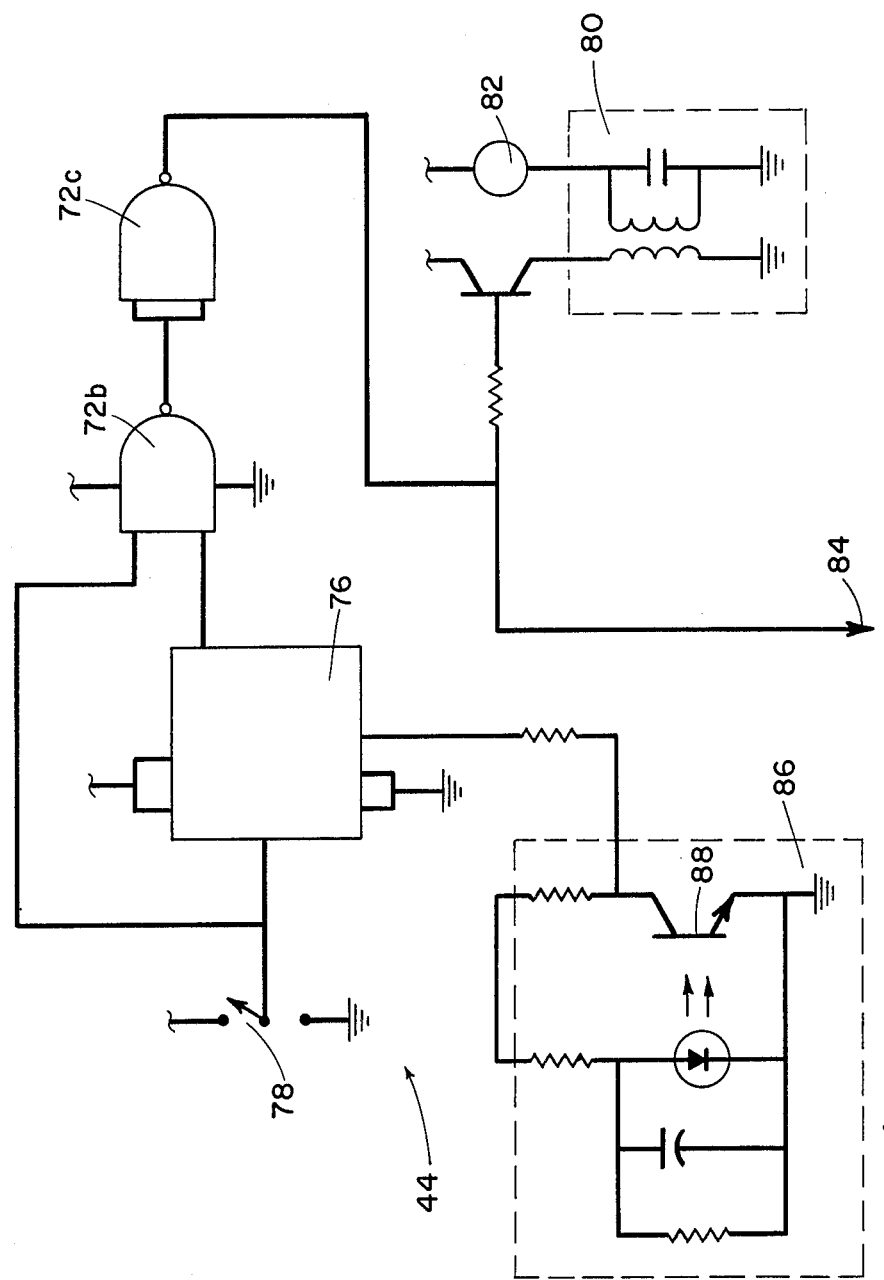
FIG. 4 is an electrical schematic diagram of the sensor circuit of FIG. 2.

FIGS. 3 and 4 jointly illustrate a preferred electrical schematic for the entire brainen 38, with FIG. 4 being particularly directed to the sensor 44. The circuits shown in FIGS. 3 and 4 are merely representative of one particular arrangement for the electronic components of the invention, but there is no intention of limiting the invention to the particular electronic circuitry shown herein.

The circuit shown in FIG. 3 includes a manual clock means 50 operably connected with suitable nangates 52a, 52b, and 52c through suitable switch means 54. The switch means 54 is operably connected with a voltage supply (not shown) which is preferably a twelve volt system, but not limited thereto. The nangates 52a, 52b and 52c are on a first common chip and are operably connected with suitable similar nangates 54a, 54b, 54c and 54d which are on a second common chip. The nangates 54a, 54b, 54c and 54d are operably connected with a suitable drive chip means 58 which is operably connected with a suitable stepper motor 60. The nangates 54a, 54b, 54c and 54d are also operably connected with a main drive means 62 through switch means 64. A plurality of nangates 66a, 66b, 66c and 66d and a third common chip are operably connected with the nangates 54a, 54b, 54c and 54d through a chip 68 which is operably connected with an automatic mode switch means 70. The switch means 70 is operably connected with the voltages source as hereinbefore set forth. The nangates 66a, 66b, 66c and 66d are also operably connected with a nangate 72a which is on a fourth chip. The nangate 72a is also operably connected with the voltage source.

The nangate 72a is on a common chip with the nangates 72b and 72c (FIG. 4) which are operably connected with a chip 76. The chip 76 is operably connected with an automatic mode switch means 78. The nangates 72b and 72c are also operably connected with a suitable relay means 80 which is operably connected with a suitable solenoid means 82. The relay means 80 is operably connected with the nangate 54b of the second chip as indicated at 84 in FIGS. 3 and 4.

The chip 76 is operably connected with a suitable photo diode sensor means 86 which includes a receptacle 88 which is preferably in the form of a light emitting diode which senses the action of the needle 24 during operation of the apparatus 10. As hereinbefore set forth, in the event the needle 24 inadvertently engages or pierces a vein and blood is sensed by the receptacle means 88, the operation of the apparatus will be aborted.

From the foregoing it will be apparent that the present invention provides a novel bio-medical injector device having a carriage apparatus slidably mounted on a base unit and carrying a hypodermic needle therewith. The needle may be prefilled or prepared with the desired medication, and is supported in an optimum angular orientation against the skin area wherein a medical injection is to take place. A motor drive means is operably connected with the hypodermic needle for actuation thereof, and a solenoid is operably connected with the carriage for effecting the reciprocation of the carriage and hypodermic needle means. Electronic circuitry is operably connected with the motor drive means and the solenoid for creating the logic necessary to perform the functions of the apparatus.

Whereas the present invention has been described in particular relation to the drawings attached hereto, it should be understood that other and further modifications, apart from those shown or suggested herein may be made within the spirit and scope of this invention.

What is claimed is:

1. A bio-medical injector apparatus comprising a base unit, carriage means reciprocally secured to the base unit, hypodermic needle means removably secured to the carriage means and movable simultaneously therewith, solenoid means carried by the base unit and operably connected with the carriage means for simultaneous reciprocation of the carriage means and hypodermic needle means, motor drive means carried by the carriage means and operably connected with hypodermic needle means for injection of the contents of the hypodermic needle means during an injection procedure, power means operably connected with solenoid means and motor drive means for supplying electrical power thereto, and electronic circuitry means including sensor means for detecting the presence of blood on the hypodermic needle means, said electronic circuitry means being interposed between the power supply means and the solenoid means and motor drive means for providing the logic required to perform the operation of the injector apparatus to stop the operation of the hypodermic needle upon detection of blood.

2. A bio-medical injector apparatus as set forth in claim 1 wherein surface means is provided on the base unit and angularly oriented with respect to the longitudinal axis of the base unit for engagement with a skin area wherein the injection procedure is to take place, the angular orientation of the surface means cooperating with the carriage means for supporting the hypodermic needle means at an optimum angular orientation for the injection procedure.

3. A bio-medical injector apparatus as set forth in claim 2 wherein the angular orientation of the surface means with respect to the longitudinal axis of the base unit is forty five degrees.

4. A bio-medical injector apparatus as set forth in claim 1 wherein the hypodermic needle means includes a housing for receiving a medication dosage therein, plunger means reciprocally disposed within the housing and movable in one direction for drawing a quantity of the medication therein and in another direction for ejecting the medication therefrom, and connecting means extending between the motor drive means and the plunger means for reciprocation thereof during an injection procedure.

5. A bio-medical injector apparatus as set forth in claim 1 wherein the electronic circuitry means comprises data input means operably connected with the power supply means, motor drive circuit means operably connected with the data input means, timer circuit means operably connected with the data input means and sensor circuit means and motor drive means, data output means operably connected with the sensor circuit means and timer circuit means and motor drive means and solenoid means.

6. A bio-medical injector apparatus comprising:
a base unit;
carriage means reciprocally secured to the base unit;
hypodermic needle removably secured to the carriage means and movable simultaneously therewith;
sensing means for detecting the presence of blood on the hypodermic needle; and,
means responsive to said sensor means for stopping the operation of the hypodermic needle upon detecting said blood.

* * * * *